United States Patent [19]

Al-Sioufi

[11] Patent Number: 4,938,758

[45] Date of Patent: Jul. 3, 1990

[54] ANTI-PATHOGENIC BLOOD COLLECTION SYSTEM AND METHOD

[76] Inventor: Habib Al-Sioufi, P.O. Box 654, Brookline, Mass. 02146

[21] Appl. No.: 121,338

[22] Filed: Nov. 16, 1987

Related U.S. Application Data

[63] Continuation of Ser. No. 848,923, Apr. 7, 1986, abandoned.

[51] Int. Cl.[5] ............................................. A61M 5/00
[52] U.S. Cl. ................................. 604/410; 604/416
[58] Field of Search ................. 604/46, 408, 410, 411, 604/416, 403, 406, 409, 414, 415, 262

[56] References Cited

U.S. PATENT DOCUMENTS 4,484,420 11/1984 Kaufman et al. .................. 604/410
4,589,867 5/1986 Israel ................................... 604/410

*Primary Examiner*—Stephen C. Pellegrino
*Attorney, Agent, or Firm*—James J. Brown

[57] ABSTRACT

A blood collection system and method are disclosed in which a neutralizing agent for pathogens such as HTLV-III virus is added to the blood collected in a standard blood bag or group of connected bags. Conveniently, the neutralizing agent, which can be in liquid or powder form, is held in a small container attached to the blood bag and released into the collected blood or alternatively, prepositioned in the collecting or satellite bag.

13 Claims, 4 Drawing Sheets

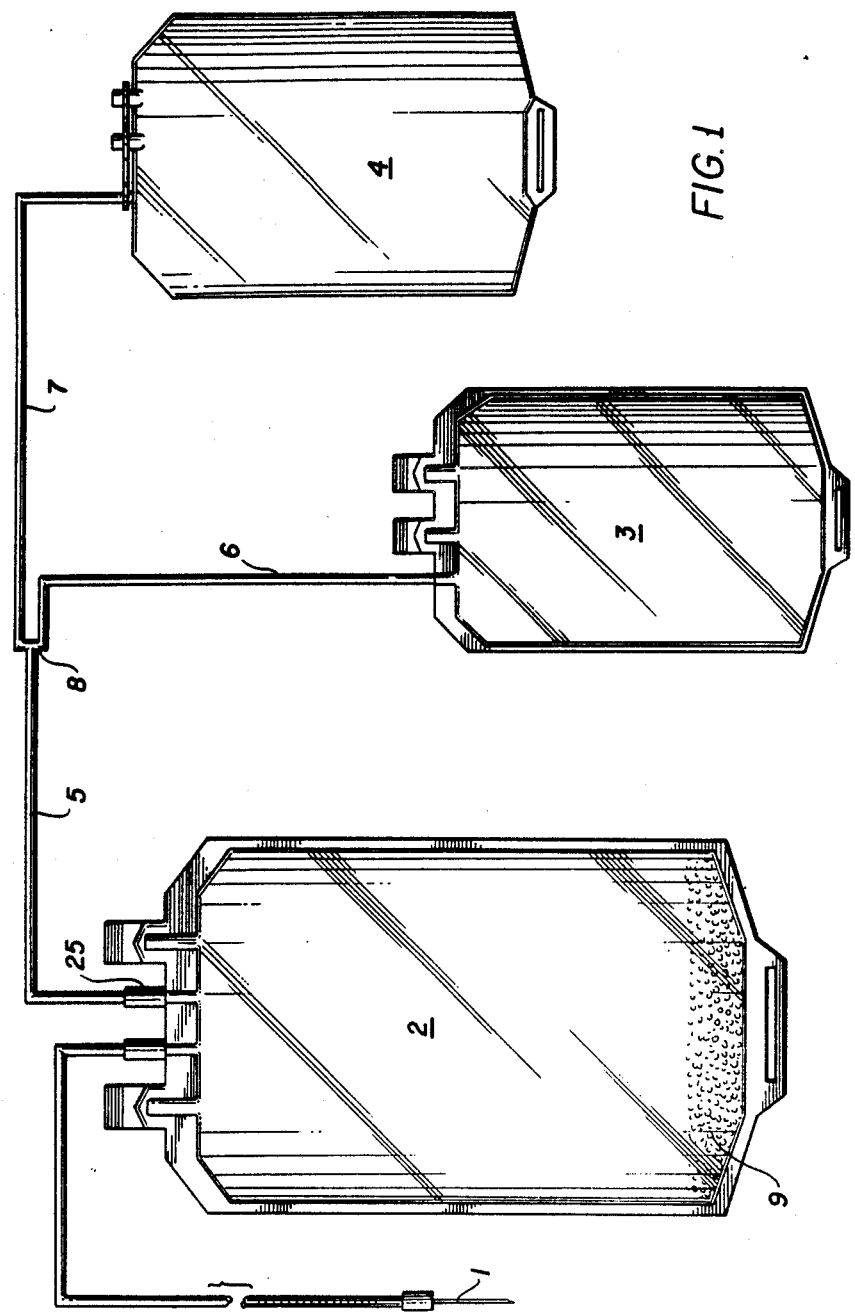

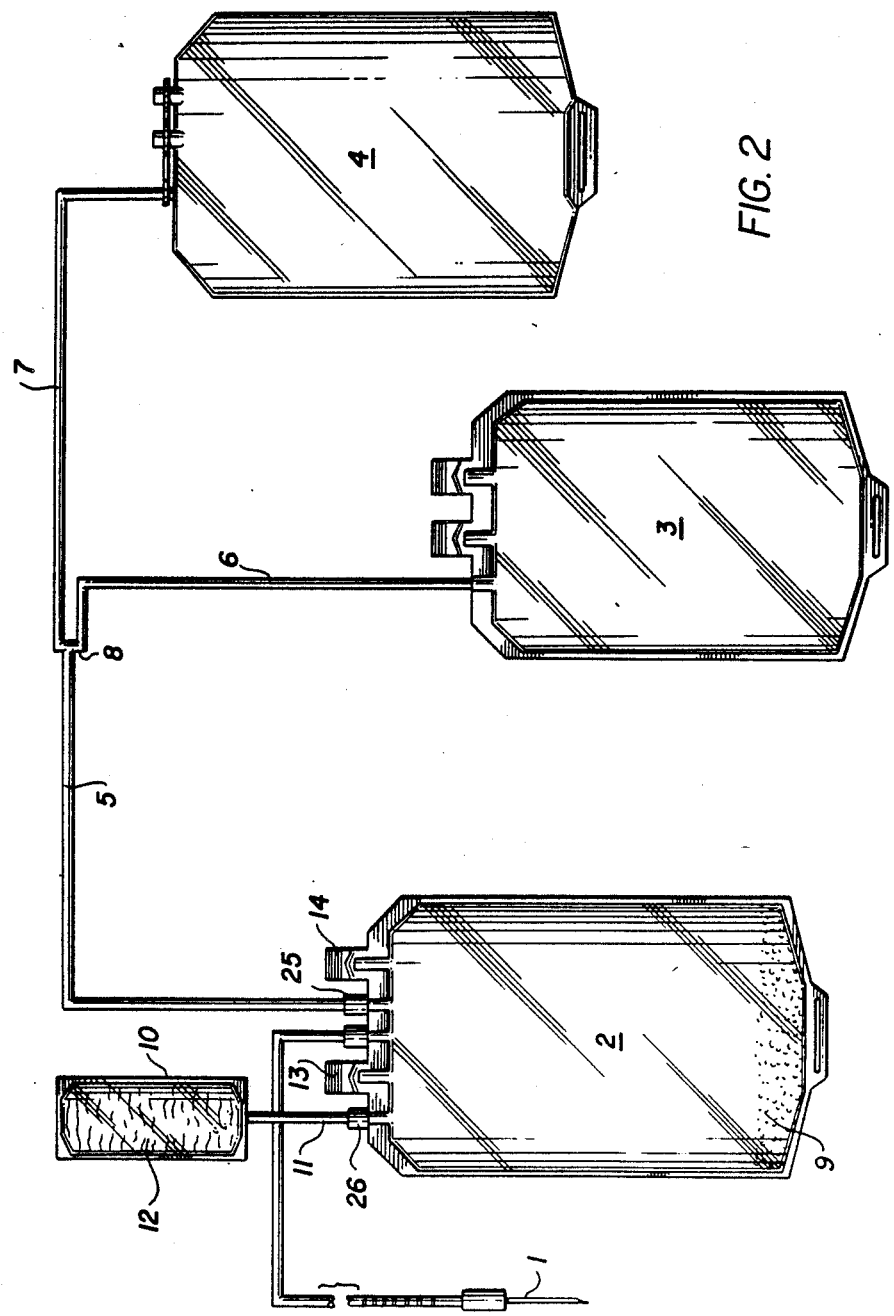

ANTI-PATHOGENIC BLOOD COLLECTION SYSTEM AND METHOD

This is an continuation of application Ser. No. 843,923 filed Apr. 7, 1986 now abandoned.

BACKGROUND OF THE INVENTION

The present invention is directed to a system and method for preventing the transmission of the family of Human T-Lymphotropic Retroviruses/Viruses (HTLV), in particular type-III, to individuals receiving blood by transfusion. The present invention is especially directed to maintaining a closed (sterile) sYstem and technique for collecting and transfusing blood components while neutralizing any Human T-Lymphotropic Retroviruses present without impairing the integrity of the system.

Recently, with the increased incidence of the deadly Acquired Immunodeficiency Syndrome (AIDS) and its causative agent, Human T-Lymphotropic Virus type-III (HTLV-III)/Lymphadenopathy-associated Virus (LAV) occurring in the general population, more and more cases of AIDS-related transfusion have been reported, (Peterman et al. JAMA, Vol. 254, No. 20, pp. 2913-2917 Nov. 22-29, 1985).

AIDS has infected over 17,000 Americans. The syndrome, caused by a virus known as HTLV-III or LAV, is spread primarily through sexual contact, sharing of hypodermic needles and transfusion. The groups at highest risk for AIDS in this country are male homosexuals and intravenous drug abusers However, a small number of cases have been caused by blood transfusion and the use of blood products such as plasma, platelets, red blood cells and coagulation factors such as Factor VIII, used by hemophiliacs. Concern for the safety of the blood supply has led the Federal Government to encourage development of a test to screen blood for antibodies to the HTLV-III/LAV virus.

The first generation of such tests, known as Enzyme-Linked Immunosorbent Assay (ELISA) tests, have recently been licensed for use in screening blood donations. These tests however, detect only antibodies for the virus and are less sensitive than screening tests that can detect the virus.

It is difficult to estimate how many AIDS cases will be avoided by screening blood. Additional complications are introduced when we consider that an individual infected with HTLV-III by a blood transfusion may, in turn, infect others, primarily sexual partners who may in turn infect still others. Thus each infection due directly to transfusion may result in numerous instances of secondary infections linked to a single transfusion event.

How frequently will a false negative test occur (Pearl et al. The Public Policy Implication of HTLV-III Antibody Screening in the Commonwealth of Massachusetts, Massachusetts Department of Health, 6/18/85 revision):

First, tests of blood from a group of individuals who although seropositive, are not detected by ELISA tests.

Second, tests, of blood from a small group of individuals who, although truly antibody negative, are virus positive. These people, although true ELISA negatives in the sense that no antibodies are present, are in a more significant sense "false negatives" since they carry HTLV-III virus.

One published study suggests that perhaps 4% of virus positive individuals are not antibody positive (Salahuddin S. Groopman J, et al. HTLV-III in Symptom-Free Seronegative persons. Lancet 1984; December 22/29: pp 1418-1420). Further preliminary work, suggests that the figure may be between 5% and 10%.

According to recent studies, it is estimated that between one to two million people are seropositive in the United States for HTLV-III virus and are most probably carriers that can transmit the virus. Because of the increased prevalence of the HTLV-III virus in the general population and its long incubation period (up to 7 years) (Peterman et al. JAMA Vol 254, No. 20 pp. 2913-2917 Nov. 22-29, 1985). AIDS-related transfusions are likely to be implicated in more and more cases. The above mentioned data reveal that current tests used to screen blood donors may reduce AIDS-related transfusions but are far from eliminating them.

Researchers at the Centers for Disease Control reported that the "The epidemiologic pattern of transmission of AIDS is strikingly analogous to that of Hepatitis B, e.g. from person to person, through sexual contact and through exposure to blood and its products" (D. Peter Drotman, JAMA, August 23-30, 1985-Vol 254, No. 8, Questions and Answers, page 1085). According to the Technical Manual of the American Association of Blood Banks, Ninth edition, 1985 page 349: "Transfusion-associated Hepatitis B decreased since blood banks switched to predominately volunteer blood and adopted mandatory Hepatitis B surface antigen (HBsAg) screening of all donors. However, despite the most sensitive tests for HBsAg detection, occasional cases of Hepatitis B continue to occur after transfusion". Clearly, more effective techniques than screening tests are needed to avoid the spread of life-threatening pathogens such as HTLV-III through transfused blood.

According to current transfusion practice, blood is collected as whole blood containing all the blood components: Plasma, Packed Red Cells, Platelets, White Cells (Leukocytes) and coagulation factors. Using different centrifugation protocols, the whole blood can then be divided into its components.

Often, at least two blood components are transfused to different patients from a single blood unit. Whole blood contains in general 40% packed red cells and 60% plasma. Once the packed red cells are separated, the blood becomes very thick and is usually diluted before transfusion.

According to the Food and Drug Administration (FDA) regulations, once the whole blood unit is collected, it is considered a closed (sterile) system and can be stored for up to seven weeks depending on the anticoagulant and preservative used. The whole blood can be manipulated within the different bags of the original unit but no additional bag can be added. Once an additional bag is connected or a sample taken from the main blood bag, the system is considered opened and the blood has to be transfused within 24 hours or be discarded.

The present invention is therefore concerned in having a permanently attached satellite container to the original blood collection unit containing an appropriate agent for neutralizing pathogens, in particular HTLV-III, in the collected blood without destroying the integrity of the closed (sterile) system.

THE PRIOR ART

*Adiministration of 3'-Azido-3'-Deoxythymidine, an Inhibitor of HTLV-III/LAV Replication, to Patients with AIDS-Related Complex*, Yarchoan et al., Lancet, pp. 575-580, Mar. 15, 1986.

*Effects of Suramin on HTLV-III/LAV Infection Presenting as Kaposi's Sarcoma or Aids-Related Complex: Clinical Pharmacology and Suppression of virus Replication In Vivo*, Broder et al, Lancet, pp. 627-630, Sept. 21, 1985.

*Ribavirin Suppresses Replication of Lymphadenopathy-Associated Virus In Cultures of Human Adult T-Lymphocytes*, McCormick et al, Lancet, pp. 1367-1369, Dec. 15, 1984.

*Suramin Protection of T-Cells In Vitro Against Infectivity and Cytopathic Effect of HTLV-III* Mitsuya et al, Science, vol. 226 pp. 172-174, Oct. 12, 1984.

*Prospects of Therapy for Infections with Human T-Lymphotropic Virus Type III* Hirsch et al, Annals of Internal Medicine, Vol. 103, pp. 750-755, November 1985.

*Selective Binding of Antipsychotics and Other Psycoactive Agents to the Calcium-Dependent Activator of Cyclic Nucleotide Phospodiesterase*, Levin et al, J. of Pharmacology and Experimental Therapeutics, vol. 209 pp. 454-459, No. 3, 1979.

*Disintegration of Retroviruses by Chelating Agents*, Wunderlich et al, Archives of virology, Vol. 73, pp. 173-183, 1982.

*Lytic Action of Neurotropic Drugs on Retroviruses in Vitro*, Wuderlich et al, Europ J Cancer 16, 1127-1132 (1980).

*Inhibition of Human T-Cell Lymphotropic Virus Type III In Vitro by Phosphonoformate*, Sandstrom et al, The Lancet, pp. 1480-82, June 29, 1985.

Prospects *Prospects of Therapy for Infections with Human T-Lymphotropic Virus Type III*, Hirsch et al, Annals of Internal Medicine. 1985; 103: 750-755.

*Antiviral effects of Phosphonoformate (PFA, Foscarnet Sodium)*, Oberg G., Pharmacology and Therapeutics, 1983; 19: 387-415.

*Antimoniotungstate (HPA 23) Treatment of Three Patients with AIDS and One with Prodrome*, Rozenbaum et al, Lancet. 1985; 1: 450-451.

*Ansamycin Inhibits Replication and Infectivity of HTLV-III/LAV* (Abstract) Anand et al. In: The International Conference of the Acquired Immunodeficiency Syndrome: Abstracts. Philadelphia: The American College of Physicians; 1985.

*Anti-AIDS Agents Show Varying Early Results In Vitro and In Vivo* Riesenberg et al. JAMA, Nov. 8, 1985-Vol 254, No. 18 pp. 2521.

U.S. Pat. No. 4,223,675 to Williams relates generally to sterile containers for solutions, being particularly suitable for blood bags within which an autoclaved liquid is stored.

U.S. Pat. No. 4,259,952 to Avoy describes a apparatus for diluting packed red blood cells contained in a transfusion bag comprising a flexible, squeezable diluent bag for containing a diluent for diluting the red blood cells in the transfusion bag.

U.S. Pat. No. 4,432,750 to Estep describes a additive solution which is used to preserve normal red cell morphology during storage. The solution comprises a concentration of a nontoxic, physiologically compatible sterol.

U.S. Pat. No. 4,435,179 to Walker discusses a blood bag assembly comprising a blood bag and means for connecting the interior of the bag with the interior of a second bag and having the improvement wherein the connecting means comprises a coupling composed of a connecting portion and a break-off point, the coupling being joined directly at the upper edge of the bag and terminates substantially evenly.

U.S. Pat. No. 4,445,889 to Wong et al describes a method for preventing an infection in a patient introduced through a indwelling catheter, the method comprising, connecting the patient to the catheter, connecting the catheter to a fluid receiving container, admitting into the container a biocidal dispensing devise, and releasing a biocide into fluid in the container for inhibiting the growth of infectious bacteria in the container and concomitantly their introduction into the catheter and the patient.

U.S. Pat. No. 4,484,920 to Kaufman discloses a container adapted for the mixing of a liquid and a solid initially placed in separate compartments. The compartment containing the solid has two access ports so liquid can pass through the compartment carrying the solid with it for better mixing.

U.S. Pat. No. 4,467,588 to Carveth provides a process for preparing an aseptic container for separately storing a sterilized powdered component and a sterilized liquid component under clean conditions.

BRIEF DESCRIPTION OF THE DRAWINGS

FIG. 1 is a representation of a standard blood collection system.

FIG. 2 illustrates the system of the present invention.

DESCRIPTION OF THE INVENTION

Figure 4:
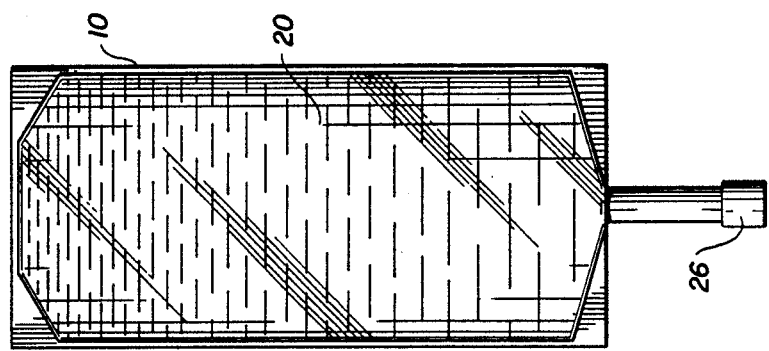
FIG. 4 illustrates in greater detail the satellite container of FIG. 2.

The present invention is directed to a device and method for preventing disease-related transfusions, especially AIDS. Conventional approaches deal with screening donors to prevent the transmission of diseases. The present invention is directed to preventing disease-related transfusions, even from infected blood units, by neutralizing the virus after collecting the blood at a temperature ranging from 1 to 37 degree centigrade, preferably at room temperature, from the donor and before infusing it to patients.

The present invention provides a new, ready-to-use system for collecting blood using an appropriate neutralizing agent in a closed system. Depending on the neutralizing agent used, either the blood will be ready for transfusion after the neutralizing agent is introduced or after use of one or more standard washing step(s) to dilute and/or remove the neutralizing agent.

In one embodiment, the present inventions utilizes commercially available blood collection units plus a new small collapsible, semi-rigid or rigid container which holds an appropriate neutralizing agent for the pathogens. The neutralizing agent can be separated from the inside of the standard 450 ml bag by different devices used in standard blood collection units. The neutralizing agent can then be introduced after the blood collection and incubated for a period of time. The standard 450 ml blood container is defined as a container where the blood is first collected into the prepositioned 63 ml anticoagulant to hold between 405 ml and 495 ml (average 450 ml) of blood.

The neutralizing agent in the container can be either a solution or a powder separated from a reconstitution solution, with both contained in the container. The neutralizing agent can be reconstituted before introducing it the 450 ml bag to mix with the whole blood. Alternatively, the neutralizing agent can be added directly to the blood collection bag as a powder and reconstituted by mixing it with either the transfused blood itself or liquid anticoagulant.

The neutralizing agent should itself be buffered to the pH of the collected blood between 7.5 and 7.4 and can, advantageously contain substances that increase the cellular permeability for the neutralizing agent such as Dimethylsulfoxide and Glycerol.

Standard blood transfusion equipment also can contain several satellite bags which are connected to the primary 450 ml blood collection bag. These satellite bags, which may be the same size or smaller than the primary bag, can be used to hold blood components such as platelets, leukocytes, plasma, blood diluents, blood preservatives or whole blood. The neutralizing agent of the invention can also be added to one of these satellite bags by means of a small attached container or pre-positioned within any bag connected to the collection unit in the manner discussed above or prepositioned in the 450 ml bag.

The present invention, accordingly provides, a new, ready to use, blood collection unit which can be any of the already commercially available units with an appropriate neutralizing agent for pathogens such as the HTLV-III virus.

Depending on the neutralizing agent that is used, an incubation period may be needed for the neutralizing agent to act and continuous mixing of the blood may be required to enhance and speed neutralization. One or more standard washing step(s) may be required to wash out and dilute the neutralizing agent. Depending on the application, the neutralizing agent will be introduced to the whole blood after collection or to a blood component separately such as packed red cells or plasma. Examples of appropriate neutralizing agents for pathogens such as HTLV-III in accordance with the invention are:

1. SURAMIN:
   Used in a total ranging from 0.02 mg to 900 mg per 450 ml
2. RIBAVIRIN: bag.
   Used in a total dose ranging from 0.02 mg to 900 mg per 450 ml
3. NEUROTROPIC DRUGS THAT INCLUDE THE FOLLOWING GROUPS:
   a. Neuroleptic Drugs such as:
      1. Phenothiazines and its derivatives such as: Chlorpromazine, Promazine, Butaperazine, Methophenazine, Fluphenazine Hydrochloride Fluphenazine Decanoate, Triflupromazine, Trifluoperazine and others.
      2. Rauwalfia alkaloids such as Reserpine.
      3. Butyrophenones such as: Haloperidol and Trifluperidol.
      4. Dibenzodiazepines such as: Clozapine.
   b. Antiemetics such as:
      1. Chlorphenethazine.
      2. Promethazine.
   c. Beta-adrenergic blockers such as Propranolol. One or more of the above mentioned Neurotropic Drugs will be used in a concentration that gives a final molarity for the drug ranging from 0.001 millimole to 100 millimoles in the 450 ml bag after the blood is collected.
4. TRISODIUM PHOSPHONOFORMATE:
   Used in a concentration that gives a final molarity for the drug ranging from 0.003 millimole to 2.0 millimoles in the 450 ml bag after the blood is collected.
5. ANSAMYCIN:
   A derivative of Rifamycin S, will be used in a concentration that gives a final molarity for the drug ranging from 0.01 micromole to 900 micromoles in the 450 ml bag after the blood is collected.
6. ANTIMONIOTUNGSTATE (HPA-23):
   Used in a total concentration ranging from 0.01 mg to 500 mg per 450 ml bag.
7. 3'-AZIDO-3'-DEOXYTHYMIDINE
   Previously referred to as Compound S, is used in a concentration that gives a final molarity for the drug ranging from 0.01 micromole to 900 micromoles in the 450 ml bag after blood is collected.
8. ETHYLENEDIAMINETETRAACETATE (EDTA) AND ETHYLENE GLYCOL BIS (2-AMINOETHYL ETHER)-N,N,N',N',-TETRAACETIC ACID (EGTA):
   Used in a concentration that gives a final molarity for the EDTA or EGTA ranging from 0.01 millimole to 900 millimoles. All are either drugs approved for human use by the Food and Drug Administration or Investigational New Drugs for human use.

One or more of the above neutralizing agents will be used independently or in combinations. An incubation period with or without continuous mixing might be required at a temperature ranging from 1 to 37 degrees centigrade, preferably at room temperature. To increase the permeability of the cellular components of the blood, either dimethylsulfoxide or glycerol can be added to either the anticoagulant in the blood bag itself or to the neutralizing agent bag.

To avoid the toxicity, if any, of the neutralizing agent, one or more washing step(s) may be needed to wash out and dilute the neutralizing agents. Since randomly transfused patients (the majority of patients) need a limited number of blood component units, the total exposure of the patient to any of the mentioned neutralizing agent is far below its toxicity level.

DETAILED DESCRIPTION OF THE DRAWINGS

In FIG. 1 a standard blood collection device of the prior art is illustrated in which a 450 ml blood collection bag 2 is provided with a 16 gauge needle 1 connected to a length of flexible tubing for transferring blood from a source to the bag 2. An additional flexible tube 5 is provided for withdrawing blood from the bag 2 and divides at 8 into tubes 6 and 7. Tube 6 provides access to a smaller satellite bag 3 and tube 7 leads into a special platelet bag 4. 63 ml of anticoagulant is provided at 9 in bag 2.

The contents of 2 is separated from access to tube 5 by an existing standard closure device 25 which can be opened by manipulation.

FIG. 2 of the drawings illustrates modification of the system shown in FIG. 1 in accordance with an embodiment of the present invention. The bags 2,3, and 4 and connecting tubes 5,6,7 as well as the anticoagulant 9 are as described above. In addition, however, a small container, 10, which can also be a flexible bag or a rigid container made, for example, of glass, is provided to hold an approximate amount of a neutralizing agent 12 for pathogens such as HTLV-III. The neutralizing agent is released into the bag 2 through tube 11. Parts 13 and 14 are standard fixtures for removing blood during transfusion. (25) and (26) are standard closure devices to connect the contents of the bags which can be opened by manipulation.

Figure 3:
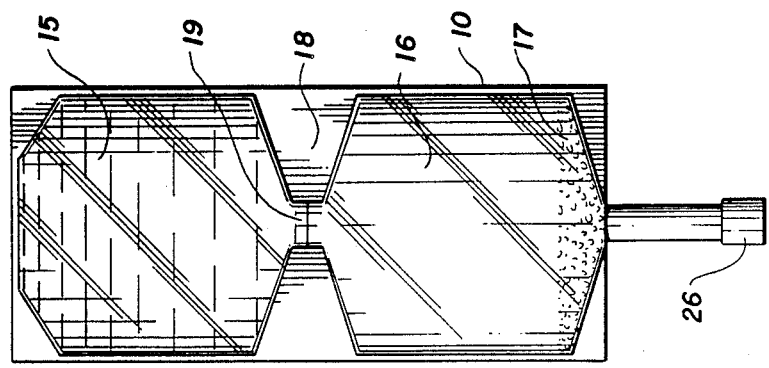
FIG. 3 illustrates an alternative container of the invention for the neutralizing agent.

FIG. 3 illustrates an alternative embodiment whereby the container 10 is divided into upper and lower compartments 15 and 16 respectively. Powdered neutralizing agent 17 is disposed in the lower compartment 16 and a solubilizing solution such as water or 0.9% Sodium Chloride is disposed in upper compartment 15. The two compartments are separated by a constriction 18 in the mid section of the container 10 and a thin membrane 19 which can be ruptured, by pressure for example, to permit mixing of the neutralizing agent and liquid just before it is displaced into the blood bag.

In FIG. 4 of the drawings the small container 10 shown in FIG. 2 is illustrated in greater detail containing a neutralizing agent 20.

Figure 5:
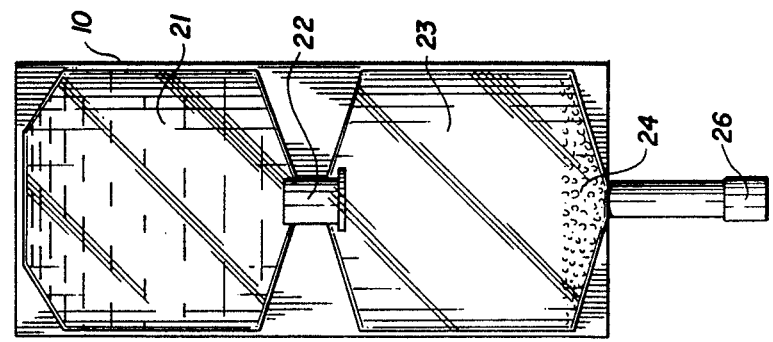
FIG. 5 illustrates an alternative to the container of FIG. 3.

In FIG. 5 of the drawings alternative configuration of the container shown in FIG. 3 is illustrated. In this embodiment the container 10 is divided into an upper compartment 21 holding a reconstituting solution and a lower compartment 23 containing a solid, liquid or powder neutralizing agent 24. A stopper 22 connects the upper and lower compartments and in such a way that it can be easily removed by applying appropriate pressure to the container. The stopper 22 thus functions essentially the same manner as the membrane 19 shown in FIG. 3.

Figure 6:
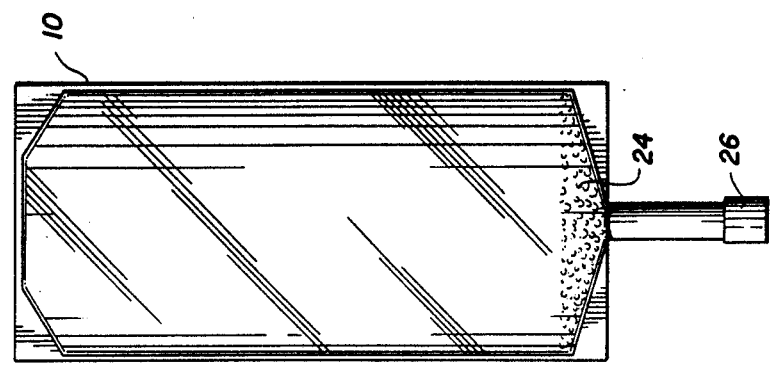
FIG. 6 illustrates yet a further alternative container of FIG. 4.

FIG. 6 of the drawings illustrates yet another embodiment of the invention in which the container 10 contains the powder neutralizing agent 24 in its base. This powder is released directly into blood bag were suitable dilution by the blood itself occurs or can be reconstituted by the anticoagulant before the blood is collected.

Figure 7:
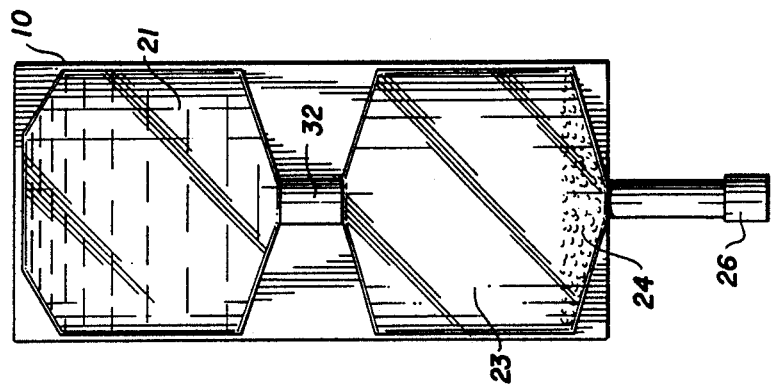
FIG. 7 illustrates another alternative to the container of FIG. 3.

In FIG. 7 of the drawings, another alternative configuration of the container shown in FIG. 3 is illustrated. In this embodiment the container 10 is divided into an upper compartment 21 holding a reconstituting solution and a lower compartment 23 containing a solid, liquid or powder neutralizing agent 24. A standard closure device 32, the same as 25 and 26, is used to connect the contents of the bags and can be opened by manipulation.

What is claimed is:

1. A blood collection system for preventing the transmission of viral pathogens in the blood which comprises: a closed blood collection container having a separate means for introducing and removing blood and a container means connected to said blood collection container for controllably introducing an effective amount of an agent for neutralizing said pathogens in the blood from said second container into the blood collection container; said neutralizing agent being selected from the group consisting of Suramin, Ribavirin, Phenothiazines, Chlorpromazine, Promazine, Butaperazine, Methophenazine, Fluphenzine Hydrochloride, Fluphenazine Decanoate, Triflupromazine, Triluoperazine, Reserpine, Haloperidol, Trifluperidol, Dibenzodiazepines, Chlorphenethazine, Promethazine, Beta-adregenic blockers, Trisodium Phosponoformate, Ansamycin, Antimonitungstate, 3'-Azido-3'-Deoxythymidine, Ethylenediaminetetraacetate (EDTA) and Ethylene Glycol Bis (2-Aminoethyl Ether)-N,N,N',N',-Tetraacetic Acid (EGTA) buffered to the ph of collected blood ranging from 6.5 to 7.4.

2. The system of claim 1 wherein said agent also contain either dimethylsulfoxide and/or glycerol in an amount effective to increase permeability of blood cell components.

3. A blood collection system for preventing the transmission of viral pathogens in the blood which comprises: a closed blood collection container having a separate means for introducing and removing blood and a container means connected to said blood collection container for controllably introducing an effective amount of an agent for neutralizing said viral pathogens in the blood from said second container into the blood collection container, said viral pathogens being a member of the family of Human T-Lymphotropic Leukemia Viruses.

4. The system of claim 3 wherein said virus is HTLV-III.

5. A ready-to-use blood collection system for preventing the transmission of viral pathogens in transfused blood which comprises: a closed system with a first blood collection container having connected therewith a means for withdrawing blood from a source and introducing it into said first container, one or more additional container means connected to said first container for receiving and holding blood or blood components from said first container, and an additional container for holding an effective amount of an agent for neutralizing pathogens in the blood connected also to said first container by a means of controllably introducing said agent into said first container; said neutralizing agent being selected from the group consisting of Suramin, Ribavirin, Phenothiazines, Chlorpromazine, Promazine, Butaperazine, Methophenazine, Fluphenazine Hydrochloride, Fluphenazine Decanoate, Triflupromazine, Trifluoperazine, Reserpine, Haloperidol, Trifluperidol, Dibenzodiazepines, Chlorphenethazine, Promethazine, Beta-adregenic blockers, Trisodium PHosphonoformate, Ansamcin, Antimoniotungstate, 3'-Azido-3'-Deoxythymidin, Ethylenediaminetetraccetate (EDTA) and Ethylene Glycol Bis (2-Aminoethyl Ether)-N,N,N',N',-Tetraacetic Acid (EGTA).

6. The system of claim 5 wherein said agent also contains either dimethylsulfoxide and/or glycerol in an amount effective to increase permeability of the cellular components of blood.

7. A ready-to-use blood collection system for preventing the transmission of viral pathogens in transfused blood which comprises: a closed system, with a first blood collection container having connected therewith a means for withdrawing blood from a source and introducing it into said first container, one or more additional container means connected to said first container for receiving and holding blood or blood components from said first container, and an additional container for holding an effective amount of an agent for neutralizing viral pathogens in the blood connected also to said first container by a means of controllably introducing said agent into said first container; said viral pathogens being a member of the family of Human T-Lymphotropic Leukemia Viruses.

8. The system of claim 7 wherein said virus is HTLV-III.

9. A blood collection system for preventing transmission of HTLV-III virus in transfused blood which comprises a first, closed, flexible, blood bag containing an effective amount of anticoagulant and having connected therewithin a means for withdrawing blood from a source and introducing it into said first bag, one or more additional blood bag means connected to said first blood bag for receiving blood or blood components therefrom and a container means connected to said first bag for holding an effective amount of a neutralizing agent for said HTLV-III virus and controllable introducing it into said first bag.

10. The system of claim 9 wherein said neutralizing agent is selected from the group consisting of Suramin, Ribavirin, Phenothiazines, Chlorpromazine, Promazine, Butaperazine, Methophenazine, Fluphenazine Hydrochloride, Fluphenazine Decanoate, Triflupromazine, Trifluoperazine, Resirpine, Haloperidol, Trifluperidol, Dibenzodiazepines, Chlorphenethazine, Promethazine, Beta-adregenic blockers, Trisodium Phosphonoformate, Ansamycin, Antimoniotungstate, 3'-Azido-3'-Deoxythymidine, Ethylenediaminetetraacetate (EDTA) and Ethylene Glycol Bis (2-Aminoethyl Ether)-N,N,N',N',-Tetraacetic Acid (EGTA).

11. The system of claim 10 wherein said neutralizing agent also contains either Dimethylsulfoxide (DMSO) and/or glycerol in an amount effective to increase penetration of blood cell component said DMSO or glycerol being prepositioned in any bag of the blood collection unit.

12. The system of claim 10 wherein said agent is a liquid.

13. The system of claim 10 wherein said container means for neutralizing agent is divided into two compartments which are separated by a means for controllably releasing the contents of one of said compartments into the and other permit mixing thereof; and one of said compartments contains said agent in powder form and the other compartment contains a liquid solubilizer for said agent.

* * * * *